United States Patent

[19]

Frantzen

[11] Patent Number: 5,873,907
[45] Date of Patent: Feb. 23, 1999

[54] ELECTROLYTIC STENT DELIVERY SYSTEM AND METHODS OF USE

[75] Inventor: John J. Frantzen, Laguna Nigel, Calif.

[73] Assignee: EndoTex Interventional Systems, Inc., Cupertino, Calif.

[21] Appl. No.: 13,862

[22] Filed: Jan. 27, 1998

[51] Int. Cl.⁶ ........................................................ A61F 2/06
[52] U.S. Cl. ................................ 623/1; 623/12; 606/191; 606/108
[58] Field of Search .................................... 623/1, 11, 12; 606/190, 191, 192, 193, 194, 195, 108

[56] References Cited

U.S. PATENT DOCUMENTS

| | | | |
|---|---|---|---|
| 5,122,136 | 6/1992 | Guglielmi et al. | 606/32 |
| 5,354,295 | 10/1994 | Guglielmi et al. | 606/32 |
| 5,423,829 | 6/1995 | Pham et al. | 606/108 |
| 5,443,500 | 8/1995 | Sigwart | 623/1 |

*Primary Examiner*—Mickey Yu
*Assistant Examiner*—Dinh X. Nguyen
*Attorney, Agent, or Firm*—Fish & Neave; Nicola A. Pisano

[57] ABSTRACT

A stent delivery system, and methods of use, are provided in which a stent is constrained in a contracted delivery state with binding straps that are electrolytically eroded to deploy the stent. The binding straps are attached to a power source and each have a small electrically uninsulated reduced thickness portion. A second electrode wire is disposed adjacent to the uninsulated areas or separately electrically coupled to an exterior surface of the patient's body. When an electric current is applied, the uninsulated areas of the binding straps are electrolytically eroded and rupture, thereby allowing the stent to at least partially deploy.

20 Claims, 3 Drawing Sheets

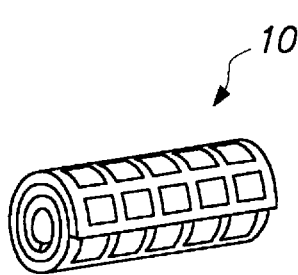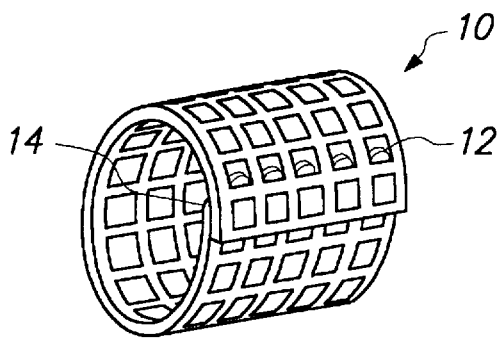
FIG. 1A     FIG. 1B
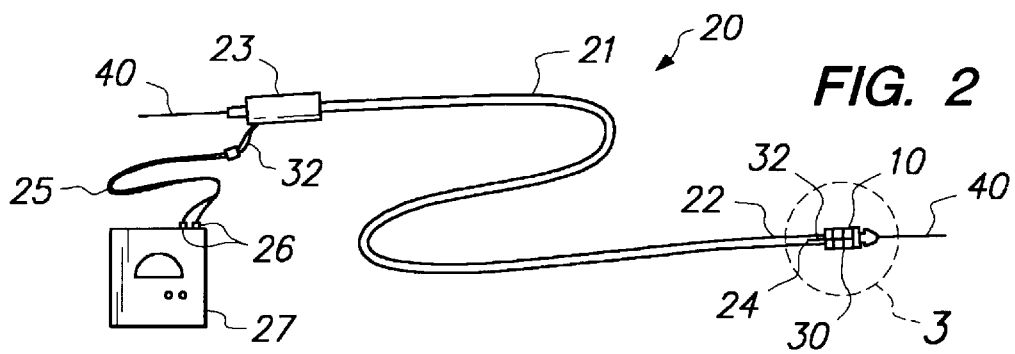
FIG. 2
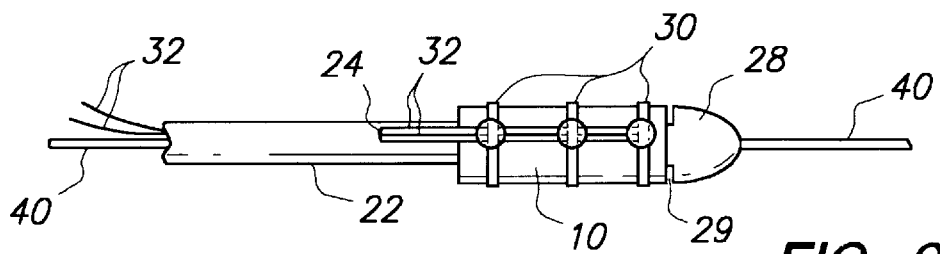
FIG. 3A
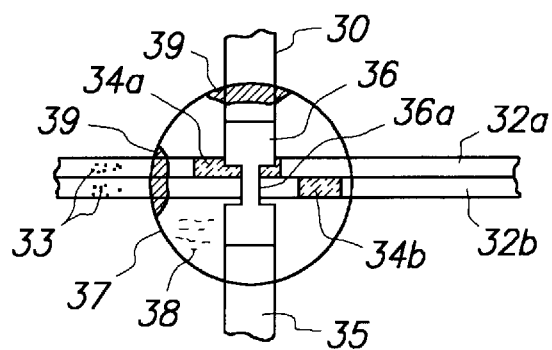
FIG. 3B

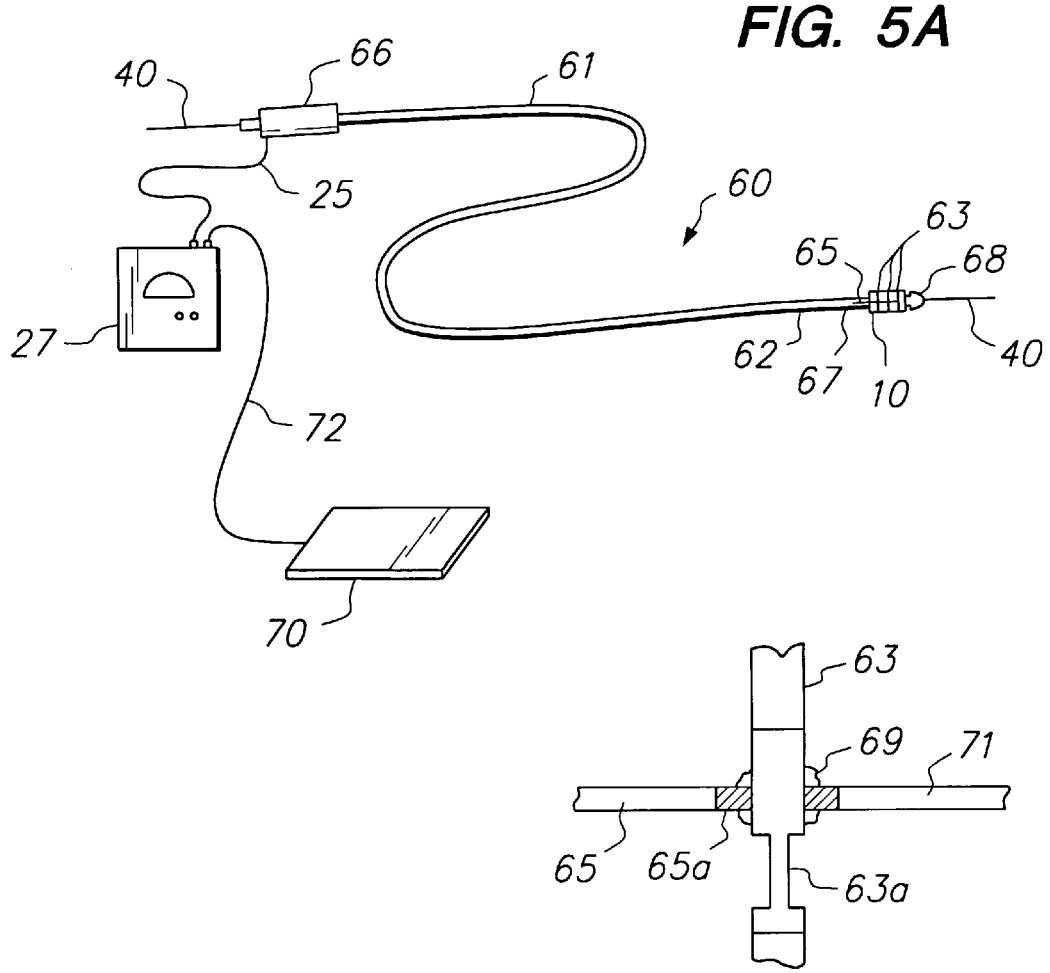
FIG. 5A
FIG. 5B
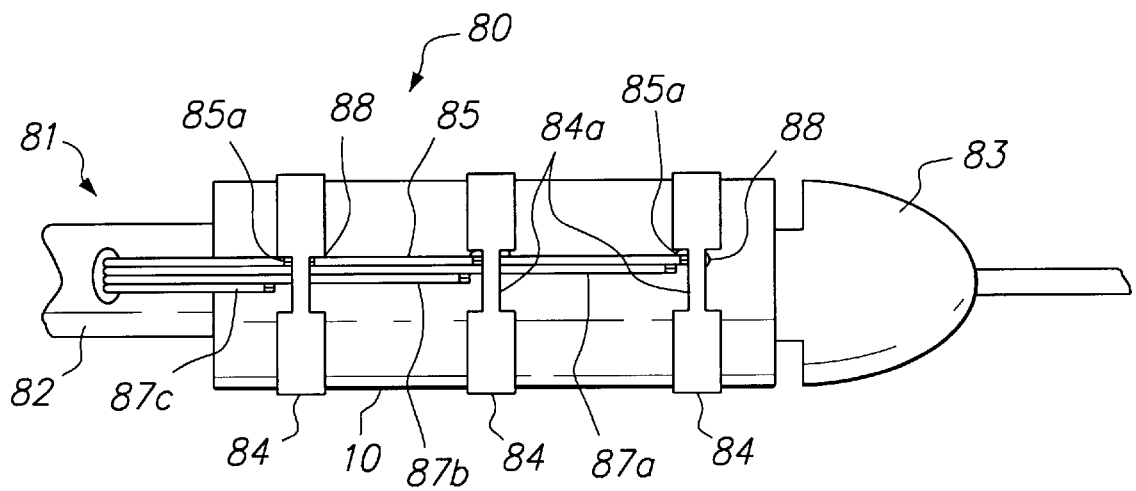
FIG. 6

ELECTROLYTIC STENT DELIVERY SYSTEM AND METHODS OF USE

FIELD OF THE INVENTION

The present invention relates generally to delivery systems for implanting endoluminal prostheses —"stents"—to treat narrowing of biological organs or vessels, for example, the coronary arteries, renal arteries and carotid arteries. More particularly, the present invention relates to methods and apparatus for releasing a stent from a contracted delivery state to a deployed state by causing electrolytic erosion of binding straps.

BACKGROUND OF THE INVENTION

In recent years a number of minimally invasive technologies have been developed to treat arterial diseases, such as atherosclerosis, which result in narrowing and stenosis of body lumens, such as the coronary arteries. Specifically, a large number of endoluminal prostheses, often referred to as "stents," have been developed to maintain the patency of a vessel, following, for example, an balloon dilatation procedure (e.g., angioplasty). These devices generally are inserted percutaneously and transluminally to the site of a constricted region in a contracted delivery state. After being positioned at a desired deployment site, the stents are then permitted to self-expand, or are balloon dilated to support the vessel or body lumen.

A drawback encountered with many previously known stents is the inability to precisely control the placement of the stent during deployment. For example, coiled sheet stents, such as described in U.S. Pat. No. 5,443,500 to Sigwart, are constrained in a contracted delivery state by a locking wire or exterior sheath, and deployed by removing the wire or retracting the sheath proximally. A disadvantage of these deployment mechanisms, however, is that the distal end of the stent expands while the proximal end is still constrained, and may result in cocking or longitudinal movement of the stent during deployment.

Similar types of stent motion may be encountered in deploying helical spring-type stents, such as described in U.S. Pat. No. 4,553,545 to Maass et al. It would therefore be desirable to provide a stent delivery system and methods that enable portions of a stent to be deployed in a predetermined sequence along the length of the stent, thereby minimizing the risk for cocking or displacement of the stent during deployment.

A further disadvantage of retractable-sheath delivery systems is that the exterior sheaths increase the overall diameter of the delivery system and reduce the ability of the delivery system to negotiate tortuous anatomy. It would therefore be desirable to provide a stent delivery system and methods that permit the thickness of an exterior sheath of the delivery system to be reduced or eliminated altogether.

SUMMARY OF THE INVENTION

In view of the foregoing, it is an object of this invention to provide a stent delivery system and methods of use that enable portions of a stent to be deployed in a predetermined sequence along the length of the stent, thereby minimizing the risk for cocking or displacement of the stent during deployment.

It is another object of the present invention to provide a stent delivery system and methods of use that permit the thickness of an exterior sheath of a delivery system to be reduced or eliminated altogether.

These and other objects of the invention are accomplished in accordance with the principles of the invention by providing a stent delivery system, and methods of use, in which a stent is constrained in a contracted delivery state with binding straps that are electrolytically eroded to deploy the stent.

In accordance with the principles of the present invention, a stent is constrained in a contracted delivery state by one or more metal straps, for example, that encircle the circumference of the stent. The binding straps preferably are attached to a power source to form an anode, and all but a small exposed area of each binding strap is covered with an electrically insulating material. A cathode is disposed adjacent to the exposed area of the binding strap, or separately electrically coupled to an exterior surface of the patient's body. When an electric current is applied, the exposed area of each of the binding straps is electrolytically eroded, thereby causing rupture and allowing the stent to at least partially deploy. The anode (and cathode, if present) and binding straps are then removed from the body.

Electrolytic erosion of the binding straps may be accomplished with an internal anode, exterior cathode, and use of the patient's body fluid as the electrolyte. Alternatively, the anode and cathode may be mounted on the stent adjacent to the exposed areas of the binding straps, with the patient's body fluid again used as the electrolyte. As a yet further alternative, the anode, and the cathode, and the exposed areas of the binding straps may be mounted on the stent adjacent to the exposed areas of the binding straps and enclosed within small balloons containing a conductive fluid.

Methods of deploying a stent by eroding a plurality of binding straps in a predetermined sequence are also provided.

BRIEF DESCRIPTION OF THE DRAWINGS

Further features of the invention, its nature and various advantages will be more apparent from the accompanying drawings and the following detailed description of the preferred embodiments, in which:

FIGS. 1A and 1B are, respectively, perspective contracted and expanded views of an illustrative stent suitable for use with the stent delivery system of the present invention;

FIG. 2 is a perspective view of a first embodiment of stent delivery apparatus constructed in accordance with the present invention;

FIGS. 3A and 3B are, respectively, a detailed view of the distal end of the apparatus of FIG. 2 within view area 3 of FIG. 2, and a view of the interconnections between a binding strap and lead wires shown in FIG. 3A.

FIGS. 4A–4C are views showing steps in the deployment of the stent of FIG. 2, while

FIGS. 5A and 5B are, respectively, a perspective view and partial detailed view of an alternative embodiment of apparatus of the present invention; and FIG. 6 is a detailed view of the distal end of another alternative embodiment of apparatus of the present invention.

DETAILED DESCRIPTION OF THE INVENTION

Figure 4A:
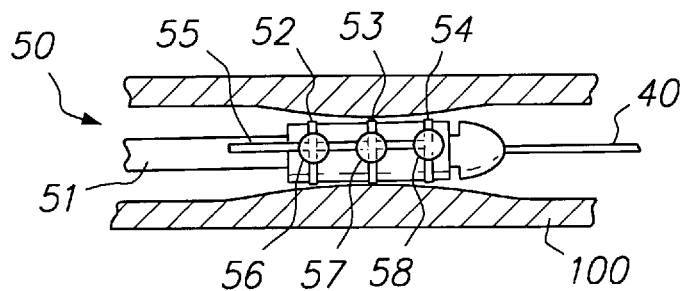

The present invention provides apparatus and methods for deploying a stent at a specified location within an artery or other body cavity or lumen. In accordance with the principles of the invention, a stent is contracted to its delivery diameter, and then constrained with metal binding straps. Once the stent is placed at a desired location within a body lumen, an electric current is applied to the binding straps that causes them to erode, thus permitting the stent to partially or fully expand to its deployed diameter.

In accordance with the principles of the present invention, electrically uninsulated areas of the binding straps are electrified in the presence of an electrically conductive fluid, which causes the exposed areas of the binding straps to erode via electrolytic action. The binding straps may be electrified as either anodes or cathodes, and a electrode of opposite polarity may be either mounted adjacent to the exposed areas of the binding straps or attached to an exterior surface of the patient. The conductive fluid may be either contained within a balloon element, or constitute the patient's body fluids.

Referring now to FIGS. 1A and 1B, a previously known stent 10 suitable for use with the stent delivery system and methods of the present invention is described. Stent 10 comprises a generally rectangular lattice of a metal alloy, such as stainless steel or a nickel-titanium alloy, having a contracted delivery diameter (shown in FIG. 1A) and an expanded deployed diameter (shown in FIG. 1B). Stent 10 preferably includes a row of locking teeth 12 along its innermost edge 14, as described, for example, in U.S. Pat. No. 5,443,500 to Sigwart, which is incorporated herein by reference. For clarity, the details of the lattice of stent 10 are omitted from FIGS. 2–6 to better illustrate the components of the delivery system of the present invention.

Referring now to FIGS. 2 and 3A, stent 10 constrained on stent delivery system 20 constructed in accordance with the present invention is described. Stent 10 is wound to its contracted delivery diameter on distal end 22 of catheter 21, and constrained in its contracted delivery diameter by binding straps 30. Catheter 21 includes a guide wire lumen, that enables the catheter to be slidingly moved along guide wire 40, and a second lumen through which electrode lead wires 32 extend from hand grip 23 to skive 24 in distal region 22. Distal end 28 of catheter 21 has a bullet-shape that assists in urging the catheter through a body vessel or organ. Distal end 28 preferably forms step 29 on catheter 21 behind which stent 10 is disposed, to reduce snagging of the distal end of the stent against tissue during percutaneous and transluminal delivery of the stent.

Electrode lead wires 32 extend from skive 24 in distal region 22 of catheter 21 and are electrically coupled to binding straps 30. The proximal ends of electrode lead wires 32 extend from hand grip 23, where they are coupled by cable 25 to terminals 26 of power supply 27. As shown in the detailed view of FIG. 3B, electrode lead wires 32 are covered along their lengths by electrical insulation 33, except for a plurality of windows 34a and 34b adjacent to each one of the binding straps. In particular, electrode lead wire 32a includes windows 34a that are positioned so that electrode lead wire 32a makes a direct electrical connection to binding straps 30. Electrode lead wire 32b, which is of opposite polarity, is also covered by electrical insulation 33 except where windows 34b are disposed adjacent to, but not in direct electrical contact with, the binding straps.

Binding straps 30 preferably are covered with electrical insulation 35 except in exposed areas 36 having reduced thickness portions 36a. Exposed areas 36 are in direct electrical contact with windows 34a of electrode lead wire 32a, and may be welded thereto. In the embodiment of FIGS. 1–3, the exposed areas 36 of binding strap 30, and windows 34a and 34b of electrode lead wires 32a and 32b, respectively, are enclosed within small balloons or bubbles 37 filled with electrolyte 38. Binding strap 30 and electrode lead wires 32 are attached to bubbles 37 at joints 39, and retain binding straps 30 mechanically coupled to bubbles 37 and electrode lead wires 32 for removal after deployment of stent 10. Joints 39 may be formed using a suitable biocompatible adhesive, such as a urethane epoxy.

Binding straps may be formed from continuous loops of material, for example, as thin slices from a hollow tube, or may be formed by welding the ends of strips of metal or metal alloy together to form closed loops. Electrode lead wires 32 and binding straps 30 preferably have a diameter in a range of 0.0005 inch (0.013 mm) to 0.002 inch (0.051 mm), while the exposed area of the binding straps preferably has a diameter of about 0.0005 inch (0.013 mm). Reduced thickness portions 36a preferably have a length of about 0.005 to 0.010 inch (0.013 to 0.254 mm). Except for windows 34a and 34b, and exposed areas 36, electrode lead wires 32 and binding straps 30 preferably are covered with about 0.0001 to 0.0002 inch (0.002 to 0.005 mm) of electrically insulating material. For use in the present invention, binding straps 30 must be capable of withstanding the tensile forces developed by the constrained stent, but reduced thickness portions 36a must be sufficiently thin that they will disintegrate by electrolytic action when exposed to an electric current (a feature referred to hereinafter as "electrolytically erodible"). Electrode lead wires 32 and binding straps 30 may be made from any of a number of metals and metal alloys, such as iron or stainless steel.

In accordance with the present invention, power source 27 is connected to electrode lead wires 32 and provides an alternating or direct current to the electrify binding straps 30. Electrode lead wire 32a, and thus binding strap 30, preferably is coupled to power source 27 to form an anode, while electrode lead wire 32b preferably is coupled to power source 27 to form a cathode. Alternatively, with appropriate modifications to the electrode lead wires and binding straps, the polarities of the electrode lead wires 32a and 32b may be reversed. Bubbles 37, which may comprise a tough and flexible plastic, such as polyurethane, enclose the exposed areas 36 of the binding straps, windows 34a and 34b of electrode lead wires 32, and an electrically conductive solution, such as saline solution.

When current is supplied to electrode lead wires 32, metallic ions move from the anode (reduced thickness portion 36a of exposed area 36) to the cathode (window 34b of electrode lead wire 32b), thereby causing erosion of the anode in exposed area 36. When this process is permitted to continue for a short period of time, on the order of 30 seconds to 5 minutes, metal loss from exposed area 36a will be sufficient to weaken the binding strap so that the radial tensile force imposed by the constrained stent causes the binding strap to rupture. For example, if power source 27 is a DC current supply, a current of approximately 1 to 2 milliamps is expected to cause an exposed area 36a having a diameter of 0.0002 to 0.0005 inch (0.005 to 0.013 mm) to erode in about 30 seconds. When the binding strap ruptures, the stent deploys to assume at least a partially expanded shape.

Figure 4B:
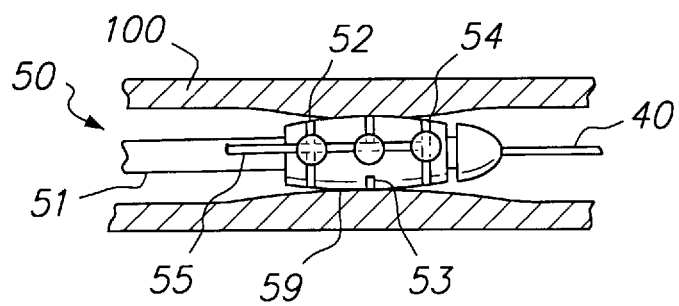

Referring now to FIGS. 4A to 4B, methods of using the above-described apparatus of the present invention to provide a predetermined sequence of rupture of the binding straps is described. In FIG. 4A, stent delivery system 50 is shown disposed in body lumen 100 on guide wire 40. Delivery system 50 has stent 10 constrained on catheter 51 by binding straps 52, 53, and 54. Binding straps 52, 53 and 54 are coupled to electrode lead wires 55 at junctions enclosed by electrolyte-filled bubbles 56, 57 and 58, as described hereinabove with respect to FIGS. 3A and 3B. In the embodiment of FIGS. 4, however, the thickness of the reduced thickness portion of the exposed area of binding strap 53 is smaller than that of binding straps 52 and 54. Thus, when a current is supplied to electrode lead wires 55, binding strap 53 will preferentially rupture before binding straps 52 and 54.

In FIG. 4A, catheter 51 and stent 10, constrained by binding straps 52, 53 and 54, is disposed in body lumen 100 following, for example, a balloon dilatation procedure. During the balloon dilatation procedure, which typically precedes stent implantation, the lumen is expanded with a balloon dilatation device to disrupt the stenosis. Positioning of stent 10 within body lumen 100 may be confirmed, for example, by a fluoroscope. One or more of binding straps 52, 53 and 54 may coated with a radioopaque material, such as gold, to assist in fluoroscopic visualization of delivery system 50 prior to stent deployment.

Once catheter 51 is positioned within the narrowed portion of body lumen 100, a current is supplied to electrode lead wires 55 that causes metal atoms to move through the electrolyte in bubbles 56, 57 and 58 from the anode (exposed area of the binding strap) to the cathode. Because the reduced thickness portion of the exposed area of binding strap 53 is thinner than the corresponding portions of binding straps 52 and 54, binding strap 53 will rupture first. Consequently, stent 10 will bow outwardly in mid-region 59 and contact the interior wall of the body lumen first in the mid-region of the stent. This feature is expected to be particularly advantageous, because during subsequent rupture of binding straps 52 and 54, prior engagement of mid-region 59 of the stent with the interior wall of body lumen 100 is expected to reduce longitudinal displacement of the stent.

Figure 4C:
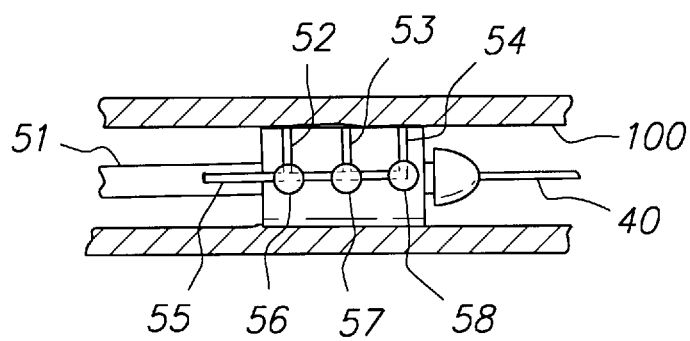
Figure 4D:
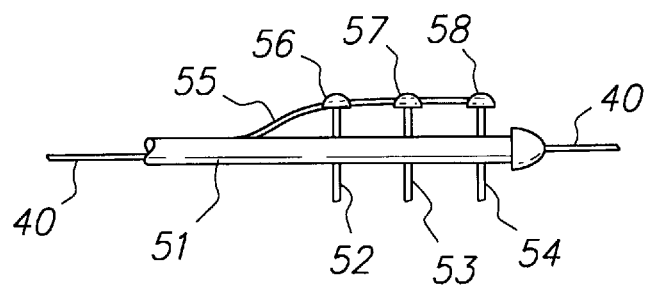
FIG. 4D is a view of the stent delivery system after it is removed from the deployment site.

Referring to FIG. 4C, when binding straps 52 and 53 rupture, either serially or simultaneously, the prior contact of mid-region 59 of stent 10 with body lumen 100 will serve to reduce or eliminate longitudinal movement of the stent. Because binding straps 52, 53 and 54 and electrode lead wires 55 are coupled to bubbles 56, 57 and 58 at the joints (see joints 39 in FIG. 3B), the ruptured binding straps remain attached to catheter 51 via electrode lead wires 55. In particular, when binding strap 53 ruptures, the end of the binding strap that is not coupled to the bubble by a joint (see FIG. 3B) slips out of the bubble, while the joint on the opposing side of bubble retains the ruptured strap coupled to the catheter for subsequent removal.

If stent 10 is of the type described in the above-referenced U.S. Pat. No. 5,443,500, the stent will only partially expand upon being released from the binding straps, and will impose a relatively small radial force on the interior wall of body lumen 100 until locked into place with a dilatation device. Accordingly, catheter 51 may be withdrawn proximally along guide wire 40 with relatively low force, leaving stent 10 in position. When removed from the body (and rotated 90° about its longitudinal axis), catheter 51 is expected to have an appearance similar to that shown in FIG. 4D. A dilatation device (not shown) may then be advanced along guide wire 40 and radially expanded to lock teeth 12 of the stent into position, as shown in FIG. 1B. Guide wire 40 is then removed from the patient, completing implantation of the stent.

Referring now to FIGS. 5A and 5B, an alternative embodiment of the delivery system of the present invention is described. Delivery system 60 has stent 10 wound to its contracted delivery diameter on distal end 62 of catheter 61, and constrained in its contracted delivery diameter by binding straps 63. Catheter 61 includes a guide wire lumen that enables the catheter to be slidingly moved along guide wire 40, and a second lumen through which electrode lead wire 65 extends from hand grip 66 to skive 67 in distal region 62. Distal end 68 of catheter 61 has a bullet-shape that assists in urging the catheter through a body vessel or organ, as in the embodiment of FIGS. 2 and 3.

As shown in FIG. 5B, electrode lead wire 65 extends from skive 67 in distal region 62 of catheter 61 and is electrically coupled to each of binding straps 63 at weld point 69. The proximal end of electrode lead wire 65 extends to hand grip 66 and is coupled by cable 25 to one terminal of power supply 27. Electrode plate 70, which is placed against an exterior surface of the patient's body, is coupled by cable 72 to the other terminal of power supply 27. Electrode lead wire 65 is covered along its length by electrical insulation 71, except in regions 65a of weld points 69 to the binding straps. Each of binding straps 63 includes an uninsulated reduced thickness portion 63a.

In accordance with another aspect of the present invention, delivery system 60 of FIGS. 5 employs the patient's body fluid, such as the blood, as the electrolyte to electrically couple the reduced thickness portions 63a of binding straps 63 to electrode plate 70. Binding straps 63, catheter 61, and electrode lead wire 65 are constructed of similar materials to those described hereinabove with respect to the embodiment of FIGS. 2 and 3.

Use of delivery system 60 to deploy a stent is also similar to that described hereinabove with respect to FIGS. 4A through 4D. Specifically, electrode plate 70 is coupled to the patient and catheter 61 is then positioned within a body lumen. Once catheter 61 is in position, power source 27 is activated to create an electrical potential between the reduced thickness portions 63a of binding straps 63 and electrode plate 70. This electrical potential induces current to flow between the binding straps and electrode plate, via the intervening tissue and body fluids, that carries metal atoms away from the reduced thickness portions of the binding straps.

After a short period of time, generally less than 5 minutes, binding straps 63 are weakened to point of rupture, resulting in partial or complete deployment of stent 10. The reduced thickness portions of binding straps 63 also may have different predetermined thicknesses, thus causing the binding straps to rupture in a predetermined sequence. Removal of the catheter and completion of the stent implantation may be as described hereinabove.

Referring now to FIG. 6, the distal end of a further alternative embodiment of a delivery system constructed in accordance with the present invention is described. Delivery system 80 includes catheter 81 similar to that of FIG. 2, including distal end region 82 having bullet-shaped tip 83. Stent 10 is secured to the exterior surface of catheter 81 by binding straps 84. A common electrode lead wire 85, typically energized to form an anode, is electrically coupled to each of binding straps 84 in uninsulated window regions 85a, for example by weld points 88. Cathode electrode lead wires 87a, 87b and 87c are disposed so that an uninsulated tip of each of the electrode lead wires is disposed adjacent to a corresponding exposed area 84a of each binding strap 84.

As in the embodiment of FIGS. 5, the embodiment of FIG. 6 omits the electrolyte-filled bubbles and instead employs the patient's body fluid as the electrolyte. Use of the delivery system of FIG. 6 is similar to that described above with respect to FIGS. 4A to 4D, except that the ruptured binding straps are retained coupled to electrode lead wire 85 by weld points 88.

As will be readily apparent to one of skill in the design of stent delivery systems, the various embodiments of the delivery system of the present invention may be used with or without a retractable exterior sheath. If a retractable exterior sheath is employed, it may be very thin, since it will not be exposed to tensile radial forces exerted by stent 10. In addition, while the foregoing discussion of the embodiments of the delivery system illustratively employ three binding straps, a greater or lesser number of binding straps may be used, depending upon the length of the stent and other factors particular to the application. Moreover, the invention may be readily implemented with forms of electrolytically erodible straps other than the binding straps illustrated hereinabove.

Accordingly, while preferred illustrative embodiments of the present invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. Apparatus for deploying a stent in a body lumen, the stent having a constrained delivery state and a deployed state wherein the stent is at least partially expanded, the apparatus comprising:

a catheter having a distal region;

a binding strap securing the stent to the distal region in the constrained delivery state, the binding strap having an electrolytically erodible region; and a first electrode lead wire affixed to the catheter, the first electrode lead wire configured to couple the binding strap to a first terminal of a power source.

2. The apparatus as defined in claim 1, further comprising a second electrode lead wire affixed to the catheter, the second electrode lead wire including an uninsulated portion disposed adjacent to the electrolytically erodible region of the binding strap, the second electrode lead wire configured to be coupled to a second terminal of the power source.

3. The apparatus as defined in claim 2, wherein the electrolytically erodible portion of the binding strap and uninsulated portion of the second electrode lead wire are enclosed within a balloon filled with an electrolyte.

4. The apparatus as defined in claim 2 wherein the apparatus is configured so that the patient's body fluids form an electrolyte electrically coupling the electrolytically erodible region of the binding strap to the second electrode lead wire.

5. The apparatus as defined in claim 1 further comprising an electrode plate electrically coupled to an exterior surface of a patient, the electrode plate configured to be coupled to a second terminal of the power source.

6. The apparatus as defined in claim 5 wherein the apparatus is configured to that the patient's body fluids form an electrolyte electrically coupling the electrolytically erodible region of the binding strap to the electrode plate.

7. The apparatus as defined in claim 1, wherein the first electrode lead wire has a diameter of between 0.0005 and 0.002 inch (0.013 to 0.051 mm) and is covered by an insulating coating.

8. Apparatus for deploying a stent in a body lumen, the stent having a constrained delivery state and a deployed state wherein the stent is at least partially expanded, the apparatus comprising:

a catheter having a distal region;

a plurality of binding straps securing the stent to the distal region in the constrained delivery state, each one of the plurality of binding straps having an electrolytically erodible region; and a first electrode lead wire affixed to the catheter, the first electrode lead wire configured to couple each one of the plurality of binding straps to a first terminal of a power source.

9. The apparatus as defined in claim 8, further comprising a second electrode lead wire affixed to the catheter, the second electrode lead wire including a plurality of uninsulated portions, each one of the plurality of uninsulated portions disposed adjacent to a corresponding one of the electrolytically erodible regions of the plurality of binding straps, the second electrode lead wire configured to be coupled to a second terminal of the power source.

10. The apparatus as defined in claim 8, wherein each one of the plurality of uninsulated portions of the second electrode lead wire and a corresponding one of the electrolytically erodible regions of the plurality of binding straps are enclosed within a balloon filled with an electrolyte.

11. The apparatus as defined in claim 9 wherein the apparatus is configured so that the patient's body fluids form an electrolyte electrically coupling each one of the plurality of uninsulated portions of the second electrode lead wire to a corresponding one of the electrolytically erodible regions of the plurality of binding straps.

12. The apparatus as defined in claim 1 further comprising and electrode plate electrically coupled to an exterior surface of a patient, the electrode plate configured to be coupled to a second terminal of the power source.

13. The apparatus as defined in claim 12 wherein the apparatus is configured so that the patient's body fluids form an electrolyte electrically coupling each one of the electrolytically erodible regions of the plurality of binding straps to the electrode plate.

14. The apparatus as defined in claim 8 wherein thicknesses of the electrolytically erodible regions of the plurality of binding straps are selected so that the binding straps rupture in a predetermined sequence.

15. The apparatus as defined in claim 8, wherein the first electrode lead wire has a diameter of between 0.0005 and 0.002 inch (0.013 to 0.051 mm) and is covered by an insulating coating.

16. A method for delivering a stent inside a body lumen of a patient, the stent having a constrained delivery state and a deployed state wherein the stent is at least partially expanded, the method comprising steps of:

providing a stent constrained by a binding strap having an electrolytically erodible region, and a power source;

electrically coupling the binding strap to the power source;

inserting the stent to a selected position within the body lumen;

applying a voltage potential from the power source to the electrolytically erodible region of the binding strap for a sufficient period of time to cause the binding strap to rupture and release the stent to the deployed state.

17. The method as defined in claim 16 further comprising a step of removing the binding strap from the body lumen after rupture.

18. The method as defined in claim 16 wherein the step of applying a voltage potential from the power source to the electrolytically erodible region of the binding strap comprises passing current through a body fluid of the patient.

19. The method as defined in claim 15 further comprising a step of providing first and second electrode lead wires, the first electrode lead wire electrically coupled to the binding strap and the second electrode lead wire having an uninsulated tip disposed adjacent to the electrolytically erodible region of the binding strap, the step of applying a voltage potential from the power source to the electrolytically erodible region comprising a step of impressing the voltage potential across the first and second electrode lead wires.

20. The method as defined in claim 19, wherein the step of applying a voltage potential from the power source to the electrolytically erodible region of the binding strap comprises passing current through a body fluid of the patient.

* * * * *

UNITED STATES PATENT AND TRADEMARK OFFICE
CERTIFICATE OF CORRECTION

PATENT NO.   : 5,873,907
DATED        : February 23, 1999
INVENTOR(S)  : John J. Frantzen It is certified that error appears in the above-identified patent and that said Letters Patent is hereby corrected as shown below:

Column 7, line 48, change " erodible portion " to -- erodible region --.

Column 8, line 22, change "claim 8" to -- claim 9 --.

Column 8, line 33, change "claim 1" to -- claim 8 --.

Column 8, line 34, change "and" to -- an --.

Column 8, line 34, change "and electrode" to -- an electrode --.

Column 9, line 5, change "claim 15" to -- claim 16 --.

Signed and Sealed this

Twentieth Day of June, 2000

Attest:

Q. TODD DICKINSON

*Attesting Officer*    *Director of Patents and Trademarks*